United States Patent
Mailyan

(10) Patent No.: US 7,878,803 B2
(45) Date of Patent: Feb. 1, 2011

(54) METHOD FOR CORRECTION OF THE FORM OF DENTAL ALVEOLAR ARCH

(75) Inventor: Pavel D. Mailyan, Yerevan (AM)

(73) Assignee: Mayadontics LLC, Novato, CA (US)

( * ) Notice: Subject to any disclaimer, the term of this patent is extended or adjusted under 35 U.S.C. 154(b) by 38 days.

(21) Appl. No.: 11/327,210

(22) Filed: Jan. 7, 2006

(65) Prior Publication Data

US 2007/0117063 A1    May 24, 2007

(30) Foreign Application Priority Data

Nov. 18, 2005    (AM) ................................ P20050208

(51) Int. Cl.
*A61C 3/00*    (2006.01)

(52) U.S. Cl. ....................................................... 433/24

(58) Field of Classification Search ................ 433/1–24
See application file for complete search history.

(56) References Cited

U.S. PATENT DOCUMENTS

| | | | | |
|---|---|---|---|---|
| 1,142,467 | A | | 6/1915 | Walker ........................ 433/21 |
| 4,026,023 | A | * | 5/1977 | Fisher ........................... 433/7 |
| 4,028,808 | A | * | 6/1977 | Schwartz ...................... 433/7 |
| 4,123,844 | A | | 11/1978 | Kurz |
| 4,468,196 | A | | 8/1984 | Keller ......................... 433/24 |
| 4,571,178 | A | | 2/1986 | Rosenberg |
| 4,573,914 | A | * | 3/1986 | Nord .......................... 433/18 |
| 4,637,796 | A | | 1/1987 | Korn ............................. 433/7 |
| 4,976,614 | A | * | 12/1990 | Tepper ........................ 433/18 |
| 5,002,485 | A | * | 3/1991 | Aagesen ....................... 433/7 |
| 5,087,196 | A | | 2/1992 | Polanco ...................... 433/21 |
| 5,096,416 | A | * | 3/1992 | Hulsink ......................... 433/6 |
| D342,318 | S | | 12/1993 | Moffat |
| 5,376,001 | A | * | 12/1994 | Tepper .......................... 433/6 |
| 5,399,087 | A | * | 3/1995 | Arndt ............................ 433/7 |
| 5,507,638 | A | * | 4/1996 | Strazielle et al. ............... 433/6 |
| 5,536,169 | A | | 7/1996 | Yousefian ...................... 433/6 |
| 5,580,243 | A | * | 12/1996 | Bloore .......................... 433/6 |

(Continued)

FOREIGN PATENT DOCUMENTS

AM    197    11/1996

(Continued)

OTHER PUBLICATIONS

A. A. Kolesov "Stomatology of childhood" Moscow 1970, pp. 452, 453 (description of Fig. 106).

(Continued)

*Primary Examiner*—Cris L Rodriguez
*Assistant Examiner*—Yogesh Patel
(74) *Attorney, Agent, or Firm*—Joshua D. Isenberg; JDI Patent

(57) ABSTRACT

A method for correction of the form of dental alveolar arch relates to medicine and can be used in orthodontics for correction of the form of dental alveolar arch in the lingual and vestibular directions. The method intensifies correction of the form of alveolar process and increases convenience of the device usage. The method may be realized through fitting of an orthodontic device in the cavity of the mouth, its periodic removal and activation and influence on teeth by forward and rotary forces. In intervals between periodic activations through repeated removal of forces developed by the device, teeth are influenced by forces of masticatory muscles.

3 Claims, 4 Drawing Sheets

U.S. PATENT DOCUMENTS

| | | | | |
|---|---|---|---|---|
| 5,697,781 | A * | 12/1997 | Ellingson | 433/18 |
| 5,769,631 | A | 6/1998 | Williams | 433/7 |
| 5,785,520 | A | 7/1998 | Carano et al. | 433/7 |
| 5,829,970 | A | 11/1998 | Yousefian | 433/7 |
| 6,032,677 | A | 3/2000 | Blechman | 128/899 |
| 6,033,216 | A * | 3/2000 | Souris | 433/7 |
| 6,435,871 | B1 | 8/2002 | Inman | 433/7 |
| 7,104,790 | B2 | 9/2006 | Cronauer | 433/6 |
| 7,192,281 | B2 | 3/2007 | Mailyan | 433/215 |
| 7,357,633 | B2 | 4/2008 | Mailyan | 433/7 |
| 2003/0104335 | A1 | 6/2003 | Chung | 433/18 |
| 2004/0009449 | A1 * | 1/2004 | Mah et al. | 433/7 |
| 2004/0013993 | A1 | 1/2004 | Ito | 433/6 |
| 2004/0048222 | A1 * | 3/2004 | Forster et al. | 433/7 |
| 2005/0019720 | A1 | 1/2005 | Harima | 433/18 |
| 2005/0037312 | A1 | 2/2005 | Uchida | |

FOREIGN PATENT DOCUMENTS

| | | |
|---|---|---|
| AM | 199 | 11/1996 |
| AM | 511 | 3/1999 |
| AM | 512 | 3/1999 |
| AM | 514 | 3/1999 |
| RU | SU1412764 | 5/2006 |
| SU | 848020 | 7/1981 |
| WO | WO 2005/048868 | 6/2005 |

OTHER PUBLICATIONS

Kishinev, *Directory on Orthodontics*, p. 178 (description of Fig. 27) and pp. 179, 179, 181, 182 (description of Fig. 28), 188 and 189.

U.S. Appl. No. 11/327,210, to Pavel D. Mailyan, filed Jan. 7, 2006.

U.S. Appl. No. 11/327,211, to Pavel D. Mailyan, filed Jan. 7, 2006.

U.S. Appl. No. 11/327,212, to Pavel D. Mailyan, filed Jan. 7, 2006.

Office Action of U.S. Appl. No. 11/327,209 issued as US patent 7,192,281.

Notice of Allowance of U.S. Appl. No. 11/327,209 issued as US patent 7,192,281.

Office Action of U.S. Appl. No. 11/327,211.

Office Action of U.S. Appl. No. 11/327,212.

The International Search Report and "The Written Opinion of the International Searching Authority" for International application No. PCT/US2006/028793.

Final Office Action of U.S. Appl. No. 11/327,212 dated Mar. 27, 2008.

Notice of Allowance in U.S. Appl. No. 11/327,211 (issued as US Patent 7,357,633) dated Feb. 4, 2008.

Non-final Office Action dated Aug. 12, 2008—U.S. Appl. No. 11/327,212.

L. S. Persin, "Orthodontia—Treatment of Dentimaxillary Anomalies", Moscow, Scientific publishing center "Inzhener" 1988, pp. 15-17—Russian version.

L. S. Persin, "Orthodontia—Treatment of Dentimaxillary Anomalies", Moscow, Scientific publishing center "Inzhener" 1988, pp. 15-17—English translation.

Office Action dated Feb. 27, 2009 for U.S. Appl. No. 11/327,212, 17 pages.

Final Office Action dated Aug. 3, 2009 for U.S. Appl. No. 11/327,212.

Office Action dated Dec. 17, 2009 for U.S. Appl. No. 11/327,212.

William R. Proffit et al., Contemporary Orthodontics, Third Edition, Chapter 8- "Orthodontic Treatment Planning: Limitations, Controversies, and Special Problems", pp. 256-259.

William R. Proffit et al,, Contemporary Orthodontics, Third Edition Chapter 22- "Combined Surgical and Orthodontic Treatment", pp. 674-691.

Final Office Action dated Jun. 8, 2010 issued for U.S. Appl. No. 11/327,212.

Handelman et al—"Nonsurgical Rapid Maxillary Expansion in Adults: Report on 47 Cases Using the Haas Expander"—Angle Orthodontist, vol. 70, No. 2, 2000, pp. 129-144.

Aldo Carano—"Effect of different force levels on the midpalatine suture"—Progress in Orthodontics, vol. 2, Issue 1, pp. 30-41, Jan. 2001—English Abstract only.

"Active Plate—Haas Expander-Fixed-Upper" download on Aug. 17, 2010 from http://www.northstardental.com/our-products-and-services/active-plates/haas-expander-fix, 2 pages.

Kiliç et al.—"A comparison of dentoalveolar inclination treated by two palatal expanders"—European Journal of Orthodontics 30 (2008) 67-72.

Dr. Steve G—"Low-Cost Nighttime Tooth Alignment: A Powerful Way to Attract New Patients!"—NightShift Ortho : Orthodontics : Straight Teeth : Retainers : Braces : Invisible Braces- download on Aug. 9, 2010 from http://www.nightshiftortho.com/doctors.html, 10 pages.

Graber- Vanasdall- Vig- "Orthodontics—Current Principle & Technique"—Fourth Edition- Chapter 3- Treatment of Patients in Mixed Dentition, pp. 547-550.

"Nitanium® Palatal Expander2TM", Ortho Organizers. 2004 Precision Orthodontics Ltd, 13 pages.

Gerson Luiz Ulema Ribeiro et al.-"Palatal Expansion With Six Bands: an alternative for young adults"—Rev. Clin. Pesq. Odontol., Curitiba, v. 5, n. 1, p. 61-66, Jan. 2009.

Robert Marzban et al.—"Slow Maxillary Expansion with Nickel Titanium"—JCO/Aug. 1999, vol. XXXIII No. 8, pp. 431-441.

Bloore Appliance Advertising, Finishing Appliances, p. 28- Spring Aligners from <http://www.greatlakesortho.com/content/files/catalogs/laboratory/1126119660.pdf> downloaded Jul. 22, 2010.

Laser Welding by LASERTEK—download on Sep. 1, 2010 from http://www.fabdent.com/lasertek/gallery_r.html.

"Fitted"—Definition and More from the Free Merriam-Webster Dictionary—download on Aug. 30, 2010 from http://www.merriam-webster.com/dictionary/fitted.

Amparo Castañer Peiro—"Interceptive orthodontics: The need for early diagnosis and treatment of posterior crossbites"—Clinical Dentistry—Interceptive orthodontics—Med Oral Patol Oral Cir Bucal 2006;11:E210-4.

William R. Proffit et al., Contemporary Orthodontics, Fourth Edition, 2007, Chapter 10- "Mechanical Principles in Orthodontic Force Control", pp. 373-377.

An English translation of a Response to the Examiners of the Russian Patent Office dated May 6, 2009 for the Russian Patent Application No. 2008105370 (International Application No. PCT/US2006/028793).

Extended European Search Report dated Oct. 27, 2009 for European Patent Application No. 06788389.2.

fitting. (n.d.). Dictionary.com Unabridged. Retrieved Oct. 19, 2010, from Dictionary.com website: http://dictionary.reference.com/browse/fitting.

Office Action dated Oct. 28, 2010 issued for U.S. Appl. No. 11/327,212.

* cited by examiner

METHOD FOR CORRECTION OF THE FORM OF DENTAL ALVEOLAR ARCH

CLAIM FOR BENEFIT OF PRIORITY OF FOREIGN APPLICATION

This application claims the benefit of priority of Republic of Armenia Patent Application No. P20050208, to Pavel D. Mailyan, filed Nov. 18, 2005 the disclosures of which are incorporated herein by reference.

CROSS REFERENCE TO RELATED APPLICATIONS

This application is also related to commonly assigned co-pending U.S. patent application Ser. No. 11/327,212 to Pavel D. Mayilyan entitled "DEVICE FOR CORRECTION OF THE FORM OF DENTAL ALVEOLAR ARCH", which is filed concurrently herewith, the disclosures of which are incorporated herein by reference. This application is related to commonly assigned co-pending U.S. patent application Ser. No. 11/327,211 to Pavel D. Mayilyan entitled "DEVICE FOR CORRECTION OF THE FORM OF UPPER JAW", which is filed concurrently herewith, the disclosures of which are incorporated herein by reference. This application is also related to commonly assigned co-pending U.S. patent application Ser. No. 11/327,209 now U.S. Pat. No. 7,192,281 to Pavel D. Mayilyan entitled "METHOD FOR STIMULATION OF GROWTH of MISSING TISSUES OF JAW DEFECTS AND A DEVICE FOR ITS REALIZATION", which is filed concurrently herewith, the disclosures of which are incorporated herein by reference.

FIELD OF THE INVENTION

The invention relates to the medicine and can be used in orthodontics for correction of the form of dental alveolar arch in the lingual and vestibular directions.

BACKGROUND

Primordially, the correction of teeth position was realized by forward influences of active details of removable orthodontic devices on teeth that was carried out by periodic removal of the device, restoration of its decreasing influences and its fitting in a cavity of a mouth.

In the beginning of the 20$^{th}$ century, Mershon and Crozat have developed devices allowing to carry out forward influences simultaneously on lingual surfaces of lateral and frontal teeth (see, "Directory on orthodontics", Kishinev 1990, page 180, FIG. 27 and page 188, FIG. 28).

At about the same time, Ainsworth designed a device, carrying out forward influence respectively on lingual and vestibular surfaces of lateral and frontal teeth (see, Kolesov "Stomatology of childhood" Moscow 1970, FIG. 106).

Today, the advanced removable devices of forward influence—appliances of Crozat-Ricketts and Wilson, are widely used in practice (see, respectively "CONSUMMATE OCCLUSION" R. Ricketts 1996, FIGS. 2-7 and "ENHANCED ORTHODONTICS" R. Wilson, W. Wilson, page 55).

The above-described devices carrying out a method of periodic activation and influence on teeth by forward forces allow to achieve correction of teeth position and form of dental arch. However, the expansion and lengthening of a dentition by the above-mentioned method results in a buccal (vestibular) inclination of teeth, that is, corpus (bodily) shifting of teeth is not provided.

In 1886, Angle, the founder of modern nonremovable orthodontic equipment designed a device of forward influence, which is nonremovably fastened on vestibular surfaces of teeth.

In 1916, for the first time he offered a method of influence by forward-rotary forces, carried out by the fixed arch device, providing corpus (bodily) shiftings of teeth. Subsequently, Angle, through improvement of a design of nonremovable orthodontic device for forward-rotary influence on teeth, has executed it in the form of arches fastened in locks, rigidly fixed on teeth. A method and devices, developed by Angle, have allowed achievement of a corpus (bodily) shifting of teeth and correction of the form of dental arch. (see, "CONSUMMATE OCCLUSION" R. Ricketts 1996, FIGS. 2-5B and 2-6A).

However, for high-grade deformations of a dental alveolar arch, achievement of corpus (bodily) shifting of teeth in vestibulolingual directions through influence of forward-rotary forces on them by fixed arch devices is possible to realize only after preliminary correction of geometry of dental arch and alignment of teeth.

As a rule, the mentioned preliminary correction is carried out by removable or nonremovable devices of forward influence, which are mounted in an oral in the initial stages of treatment. This means that the process of correction of a dental alveolar arch is multistage, and the forward-rotary influences on teeth by nonremovable arch devices are carried out at later stages of orthodontic treatment.

As is well known, the movement of teeth in an alveolar process is possible due to the coordinated processes of resorption and regeneration (apposition) of an alveolar bone. Moreover, the surface of alveolar process faced to a root of tooth in places of squeezing and tension of walls of bone-medullar cavities is periodically subjected respectively to resorption and apposition.

The application of large forces in nonremovable arch devices can result in resorption of not only alveolar bone, but roots of teeth too, therefore in practice, small forces are used more often. Summarizing the above-mentioned, it should be stated that nonremovable arch devices do not ensure intensive correction of the form of alveolar process and require a long-term treatment.

For elimination of staged treatment at the high-grade deformations of a dental alveolar arch, the removable designs of orthodontic devices providing forward and rotary forces on teeth were offered. Devices of the given design constitute the metal wireframes on dentition's segments, which are dispersed along the height of teeth and connected with each other by orthodontic arches and/or springs (see the invention patent of the Republic Armenia No. 512, IPC A61C7/00, 1999, and applications for the inventions of the Republic Armenia No. 20050147, 20050148, 20050149 IPC A61C7/00, 2005). The above-described devices were applied by a method attributable to removable devices—by periodic removal of the device, restoration of decreasing influences and its fitting.

Such a method of treatment with the specified devices is favourably distinguished from known subjects, that at significant deformations of a dental alveolar arch, it allows to exclude multistage nature of a treatment and to achieve forward-rotary influence on all teeth in the necessary direction. Regardless of the fact that during the use of these devices the generally accepted in orthodontics values of forces on crowns of separate teeth of 50-150 gm were applied, torques on root apexes of teeth exceeded similar values provided by other devices of forward-rotary influence in several times. It is stipulated by that the fastening metal wireframes with elements, dispersedly mounted along the height of teeth's crowns, at realizing of rotary influence on teeth provide the maximum large arm of applied forces and promote the increase of torque on roots of teeth. The above-mentioned property allows movement of an axis of rotation of teeth to the root apexes and, consequently, to create zones of a tension and squeezing of an alveolar bone, which are adjacent to the lingual and vestibular surfaces of roots of teeth. Depending on an axial position of teeth, the value, sequence and combination of applied forward and rotary forces on them are adjusted during their movement. The application of the above-mentioned method and devices provides a corpus (bodily) shifting of teeth and a simultaneous growth of an alveolar process dimension, with the intensity of about 0.3-0.4 mm/months. However, in the result of long-term influence of elements of fastening metal wireframes, mounted in interdental spaces, the teeth are influenced by the forces pushing out of them from the alveolar sockets that results in loosening of separate teeth.

SUMMARY

The task of the proposed method is the intensification of correction of the form of alveolar process and increase of a convenience of the device usage.

According to an embodiment of the invention the form of the dental alveolar arch may be corrected by fitting a wireframe device to a patient's teeth and periodically removing the device from the patient's teeth and activating the device to exert forward and rotary forces on the patient's teeth by means of one or more metal wireframes of the device. In intervals between periodic activations of the device the device may be repeatedly removed from the patient's teeth at least once a day, during a food assumption, to influence teeth with another kind of forward and rotary forces exerted by masticatory muscles and directed towards alternating change of zones of squeezing and tension of the periodontium.

BRIEF DESCRIPTION OF THE DRAWINGS

The nature of the invention is explained by graphic materials, where the zones of squeezing (designated by a "−" sign) and tension (designated by a "+" sign) of an alveolar process, which are formed under influence of a metal wireframes comprising lingual details (A) and vestibular details (B) and (C), which are dispersedly mounted along the height of a tooth, are depicted on FIGS. 1, 2.

The zones of squeezing and tension of an alveolar process in the case of removal of forces exerted by the device, i.e. the wireframes comprising details (A), (B) and (C), as well as partial return of a tooth to an initial position are represented on FIG. 3.

Figure 4:
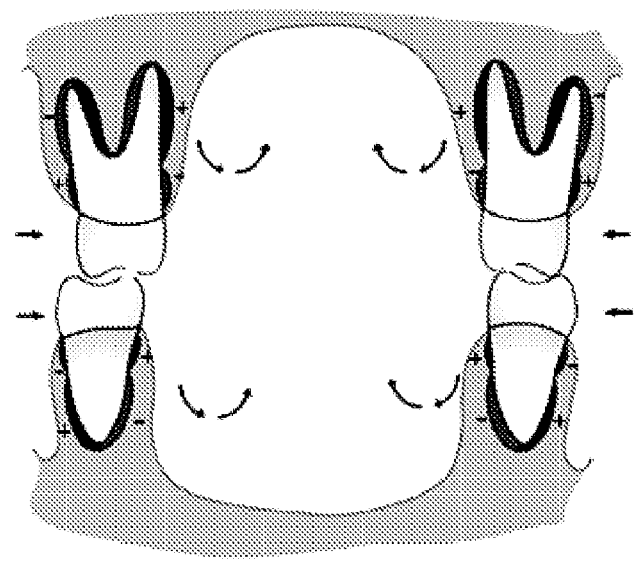
Figure 5:
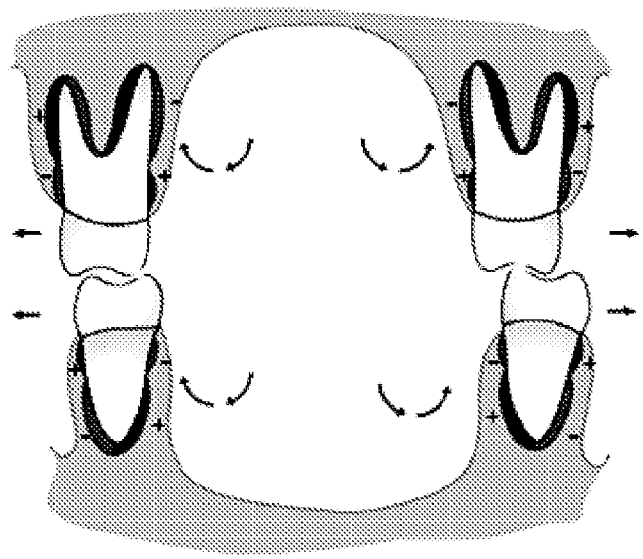
Figure 7C:
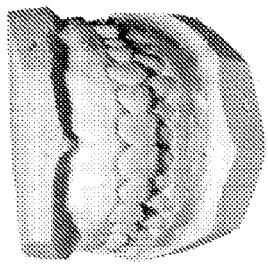
Figure 7A:
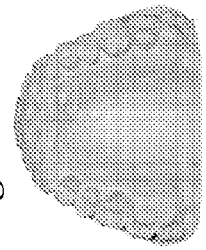
Figure 7B:
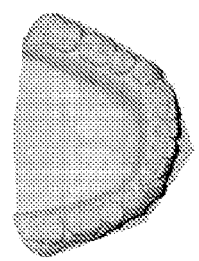
Figure 7D:
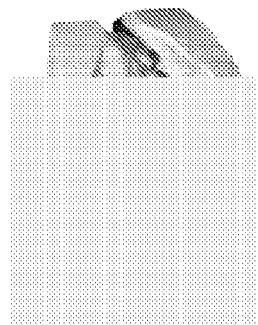
Figure 6C:
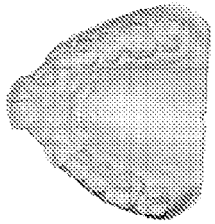
Figure 6D:
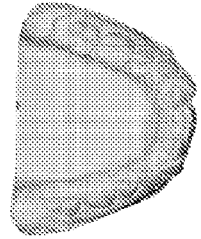
Figure 6A:
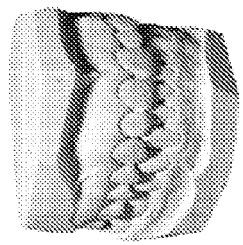
Figure 6B:
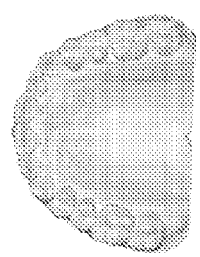

Alternating changes of zones of squeezing and tension under influence of forces of masticatory muscles are depicted on FIGS. 4, 5.

In addition, jaw models of patients before and after orthodontic treatment in accordance with the examples of particular execution of a method, which are cited below, are represented in FIGS. 6A-6D, 7A-7D.

Figure 8:
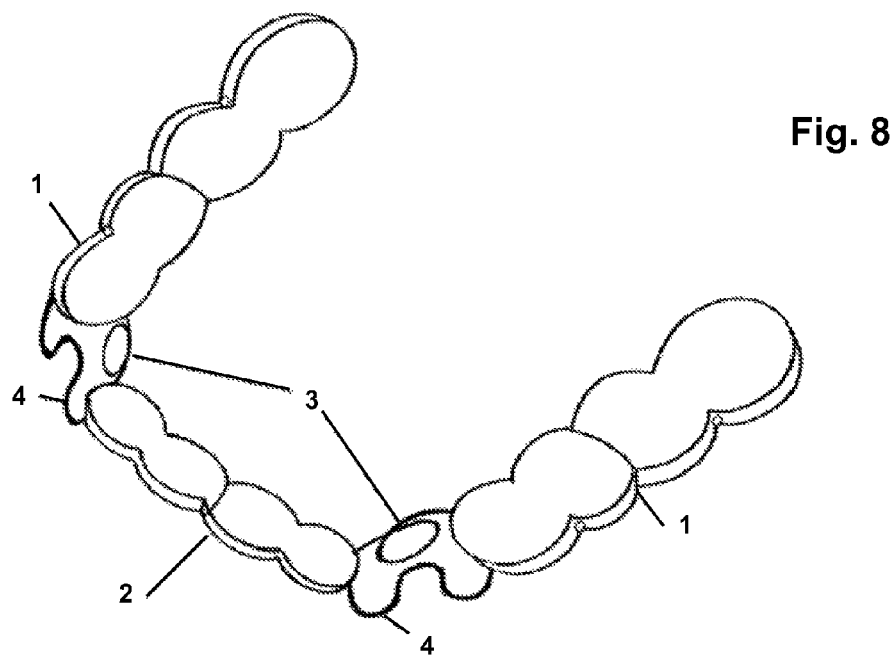
Figure 9:
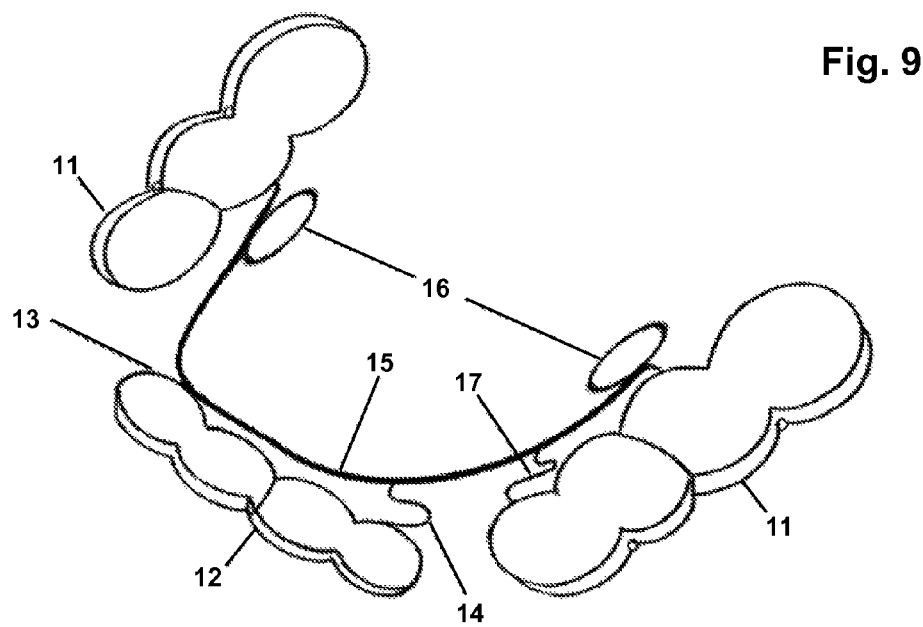

FIGS. 8, 9 are diagrams of devices for correction of the form of dental alveolar arch that may be used in conjunction with embodiments of the present invention.

DETAILED DESCRIPTION

Figure 1:
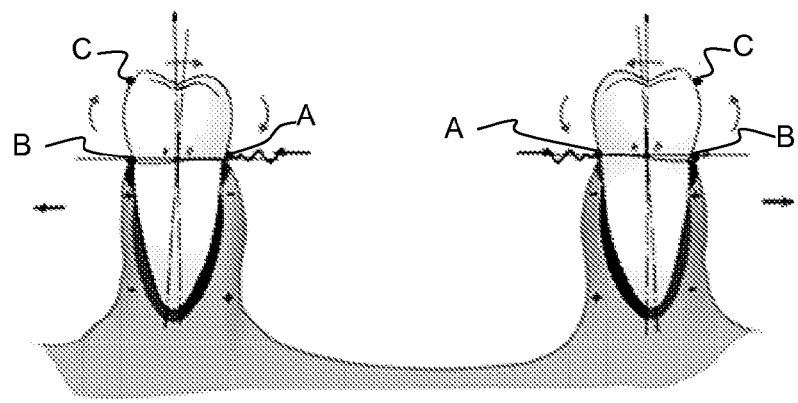
Figure 2:
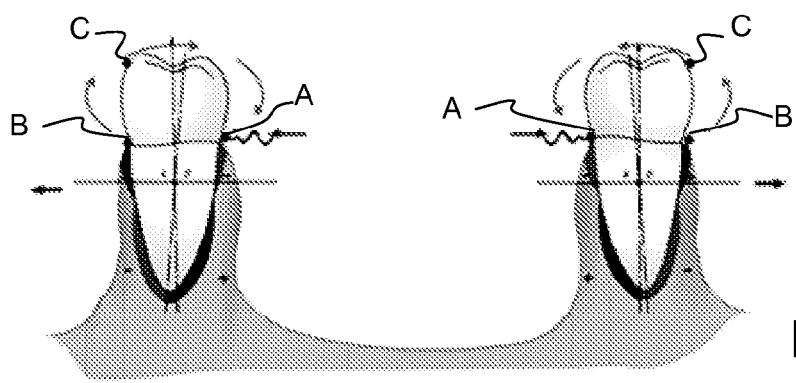

It is well known that a tissue of alveolar process is a viscous-elastic medium. The tissues of alveolar process (more precisely, periodontium) relatively well tolerate vertical loadings and much worse—horizontal. At the application of forward and rotary forces to a crown of tooth, depending on their value and position of points of their application, the axes of rotation of teeth may be disposed within the range of crowns of teeth (see, FIG. 1), and roots of teeth too (see, FIG. 2).

Figure 3:
Figure 3:
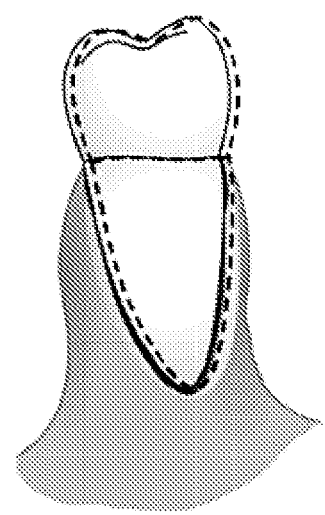

In the result of influences of forward and rotary forces on teeth, a squeezing of tissues of alveolar process by roots of teeth in horizontal direction occurs that results in its elastic deformation and movement of a tooth. The periodic removal of the device results in partial return of a tooth to an initial position (see, FIG. 3). Changes of directions of forward-rotary forces taking place at the act of chewing promote intensive alternating change of zones of squeezing and tension of the alveolar process (see, FIGS. 4, 5). The repeated removals of influences of forward and rotary forces from the teeth between periodic activations of the device, which are combined with an intensive alternating change of zones of squeezing and tension of the alveolar process at the chewing act, stimulate intensive growth of a bone tissue of alveolar process. Moreover, the frequent removals of the device or its active elements from a cavity of mouth reduce influences of elements of fastening metal wireframes on teeth that push out the latter from an alveolar socket, increase forces of masticatory muscles on separate teeth at the chewing act, and consequently, prevent a loosening of separate teeth.

The efficiency of treatment by a proposed method was controlled by periodic measurement of transversal dimensions of a dental arch and an alveolar process of the patients. The measurements were performed between buccal tubercles of $4^{th}$ teeth and mesial-buccal tops of $6^{th}$ teeth, as well as, points disposed below the latter on 10 mm. The carried out investigations have shown that in the result of use of the proposed method and devices the increases of the dimensions of dental arches and alveolar processes of both jaws are occurred, with an average intensity of 2 mm/months. Movements of teeth with a similar intensity by other methods of forward-rotary influence on teeth usually result of denudation of roots of teeth (because of scarcity of bone tissue of an alveolar socket).

In the case of small height of crowns of primary and permanent teeth and their not apparent equator, the method may be realized by devices with the combined details of fastening elements. As variants of embodiment of the mentioned fastening elements may be fixed parts, in the form of fastening units, which are directly glued on separate teeth or fixed on orthodontic rings, on which metal wireframes, clasping dentition's separate segments are fixed by a maximum simplified process of removal and mounting of a device. The removal of exerted forces on teeth is carried out by a withdrawal of the device or its active elements from a cavity of mouth.

As shown in FIG. 8, a device for correction of the form of dental alveolar arch, in accordance with a first variant of the execution, has fastening elements (1) in the form of metal wireframes clasping teeth of dentition's lateral segments and a metal wireframe (2) mounted on a teeth of dentition's frontal segment, which is connected with fastening elements by lingual springs (3) and/or vestibular springs (4).

After fitting of the device of FIG. 8 in a cavity of mouth, the patient is trained on peculiarities of treatment with it. The first removal and activation of the device is usually carried out after 3 days of its fitting. The device may be periodically removed and reactivated every 15-20 days. As mentioned above, every periodic removal of the device results in partial return of a tooth to an initial position (see, FIG. 3). The activation of the device may be achieved through an appropriate deformation of the lingual springs (3) and/or the vestibular springs (4) in such a way that the wireframes (1) and/or (2) can exert forward forces on the patient's teeth in sagittal and/or transversal directions, as well as turning of metal wireframes of lateral segment fastening elements (1) and/or frontal segment fastening elements (2) around of their respective longitudinal axes in such a way that wireframes (1) and/or (2) could exert rotary forces (or torque) on the patient's teeth Then in accordance with an embodiment of the invention, a device of the type shown in FIG. 8 may be repeatedly removed from the patient's mouth cavity at least once a day, e,g, during a food assumption. With the device removed, at the act of chewing the teeth are influenced by another kind of forward and rotary forces, which are exerted by the patient's masticatory muscles. It is noted that at the act of chewing, the directions of the forward-rotary forces developed by the masticatory muscles continually change. Consequently, an intensive alternating change of the zones of squeezing and tension of the alveolar process occurs. As a result, the combination of the above mentioned steps of the proposed method stimulates an intensive growth of a bone tissue of the alveolar process.

As shown in FIG. 9, a device for correction of the form of dental alveolar arch, in accordance with a second variant of the execution, has fastening elements (11), in the form of metal wireframes clasping teeth of dentition's lateral segments and a metal wireframe (12) mounted on teeth of dentition's frontal segment. The latter is connected directly (13) and/or through spring (14) with a lingual arch (15), the ends of which are fixed on fastening elements (11). The lingual arch (15) has activation units (16) and is additionally connected with one or two fastening elements (11) through springs (17). After fitting of the device in a cavity of a mouth, the patient is trained on peculiarities of treatment with it. The device is activated every 15-20 days. By activation of the lingual arch (15), its activation units (16), as well as springs (17) and (14) accordingly disposed between the lingual arch (15) and wireframe fastening elements (11) and (12) in sagittal and/or transversal directions, as well as, in combination and alternation (proceeding from the clinical indications) with turning of metal wireframes of fastening elements (11) and frontal segment (12) around of their longitudinal axis a correction of the form of dental alveolar arch is achieved.

As shown in FIG. 9, a device for correction of the form of dental alveolar arch, in accordance with a second variant of the execution, has fastening elements (11), in the form of metal wireframes clasping teeth of dentition's lateral segments and a metal wireframe (12) mounted on teeth of dentition's frontal segment. The latter is connected directly (13) and/or through spring (14) with a lingual arch (15), the ends of which are fixed on fastening elements (11). The lingual arch (15) has activation units (16) and is additionally connected with one or two fastening elements (11) through springs (17). After fitting of the device in a cavity of a mouth, the patient is trained on peculiarities of treatment with it. The device is activated every 15-20 days. The activation of the device may be achieved through a deformation of the lingual arch (15), its activation units (16), as well as springs (17) and (14) accordingly disposed between the lingual arch (15) and wireframes (11) and (12) in such a way that wireframes (11) and/or (12) could exert forward forces on the patient's teeth in sagittal and/or transversal directions, as well as, through turning the metal wireframes (11) and/or (12) around of their longitudinal axis in such a way that wireframes (11) and/or (12) could exert rotary forces (or torque) on the patient's teeth. Then in accordance with an embodiment of the invention, the above-mentioned step of repeated removal of the device from the patient's mouth cavity at least once a day, during a food assumption may be performed.

EXAMPLES

A patient of 18 years old with the complaints related to cosmetic defect has addressed to clinic. Objectively: deep overbite, constriction of both dental alveolar arches, overcrowding and rotation of incisors of both jaws. The devices for correction of the form of dental alveolar arches have made and fitted in the cavity of patient's mouth. The first activation of devices was carried out after 3 days of their fitting. Subsequent activations were carried out after every 20-25 days. The patient was recommended to remove a device at least once a day, during a food consumption. After 3 months from the beginning of treatment, the increase of alveolar processes in the area of $4^{th}$ teeth was achieved, on the upper jaw on 5 mm, and on the lower jaw on 6 mm. The relation of dentitions and positions of teeth were normalized. For securing the results of treatment, the permanent bearing of the device in the course of 1.5 months and its removal during a food assumption, and its subsequent night bearing in the course of 2 months was recommended. The control inspections were carried out in each month, and after 4 months from the termination of a retention period the inspection has shown steady results of orthodontic treatment (see FIGS. 6A-6D).

A patient of 21 years old with the complaints to cosmetic defect has addressed to clinic. Objectively: a deep overbite, constriction of both dental alveolar arches, overcrowding and rotation of incisors of both jaws and protrusion of upper central incisors. The devices for correction of the form of dental alveolar arches have made and fitted in the cavity of patient's mouth. The first activation of devices was carried out after 3 days of their fitting. Subsequent activations were carried out after every 20-25 days. The patient was recommended to remove a device at least once a day, during a food consumption. After 4 months from the beginning of treatment, the increase of alveolar processes in the area of $4^{th}$ teeth was achieved, on the upper jaw on 6 mm, and on the lower jaw on 7 mm. The relation of dentitions and positions of teeth were normalized. For securing the results of treatment, the permanent bearing of the device in the course of 2 months and its removal during a food assumption, and its subsequent night bearing in the course of 2 months was recommended. The control inspections were carried out in each month, and after 3 months from the termination of a retention period the inspection has shown steady results of orthodontic treatment (see FIGS. 7A-7D).

The method was also successfully used as a treatment of periodontosis.

What is claimed is:

1. A method for correction of the form of dental alveolar arch, comprising:
    fitting a wireframe device to a patient's teeth, wherein the wireframe device includes two or more fastening elements, which are in the form of metal wireframes configured to clasp teeth of dentition's different segments and connected to each other through an orthodontic arch and/or through springs, wherein the wireframe device includes two or more separate wireframe segments respectively adapted to surround two or more separate dentition segments, wherein the orthodontic arch and/or springs include multiple activating units configured to exert forward and rotary forces on the wireframe segments that are transmitted to the dentition segments;
    periodically removing the device from the patient's teeth and activating the device while the device is removed to exert forward forces on the patient's teeth in sagittal and/or transversal directions through a deformation of said orthodontic arch and/or springs and rotary forces on the patient's teeth through turning of one or more of the metal wireframes of the device around their longitudinal axes in such a way that the wireframes can exert a torque on the patient's teeth; and, in intervals between periodic activations of the device, repeatedly removing the forces of the device from the patient's teeth by the patient at least once a day, during a food consumption to influence teeth with another kind of forward and rotary forces exerted by masticatory muscles and directed towards alternating change of zones of squeezing and tension of the periodontium, wherein repeated application of the forward and rotary forces and the other kind of forward and rotary forces stimulate growth of bone tissue that changes the form of the patient's dental alveolar arch.

2. The method of claim 1 wherein the two or more separate wireframe segments include first and second wireframe segments respectively adapted to surround first and second lateral dentition segments and a third wireframe segment adapted to surround a frontal dentition segment.

3. The method of claim 1 wherein the wireframe device exerts forces on the crowns of separate teeth of between 50 and 150 grams.

* * * * *